United States Patent [19]
Ramadoss et al.

[11] Patent Number: 6,048,847
[45] Date of Patent: Apr. 11, 2000

[54] USE OF BETULINIC ACID AND ITS DERIVATIVES FOR INHIBITING CANCER GROWTH AND A METHOD OF MONITORING THIS

[75] Inventors: Sunder Ramadoss, New Delhi; Manu Jaggi, Gurgaon Haryana; Mohammad Jamshed Ahmad Siddiqui, Ghaziabad, all of India

[73] Assignee: Dabur Research Foundation, Ghaziabad, India

[21] Appl. No.: 09/040,856

[22] Filed: Mar. 18, 1998

[30] Foreign Application Priority Data

Sep. 30, 1997 [IN] India ............................. 2801/DEL/97

[51] Int. Cl.$^7$ ........................... C07J 53/00; A61K 31/15; A61K 31/21; A61K 31/56
[52] U.S. Cl. ......................... 514/169; 514/510; 514/639; 514/908; 552/510
[58] Field of Search ............................ 552/510; 514/169, 514/510, 639, 908

[56] References Cited

U.S. PATENT DOCUMENTS

| | | | |
|---|---|---|---|
| 5,679,828 | 10/1997 | Lee et al. | 560/116 |
| 5,843,974 | 12/1998 | Swift | 514/370 |
| 5,869,535 | 2/1999 | Pezzuto et al. | 514/640 |

FOREIGN PATENT DOCUMENTS

| | | |
|---|---|---|
| 1143832 | 6/1989 | Japan . |
| 9426695 | 11/1994 | WIPO . |
| 9504526 | 2/1995 | WIPO . |
| 9629068 | 9/1996 | WIPO . |
| 9639033 | 12/1996 | WIPO . |

OTHER PUBLICATIONS

Fujioka, et al, Journal of Natural Products, vol. 57, No. 2, Feb. 1, 1994, pp. 243–247.
Hashimoto, et al, Bioorg. Med., Chem., vol. 5, No. 12, 1997, pp. 2133–2143.
Konoshima T. et al., Journal of Natural Products, vol. 50, No. 6, Nov. 1, 1987, pp. 1167–1170.
Miles, D. H., et al., Journal of Pharmaceutical Sciences, vol. 63, No. 4, Apr. 1, 1974, pp. 613–615.
J.S. Lee, et al., Chemical Abstracts + Indexes, vol. 125 No. 19, Nov. 4, 1996, p. 58.
Bishay, D.W. et al., Bulletion of Pharmaceutical Sciences, vol. 10, Part 2, Jan. 1, 1987, pp. 1–20.
Toda, A. et al, Chemical Abstracts, vol. 127, No. 2, Abstract 023542, Jul. 14, 1997.
Pradhan, B.P., et al, Indian J. Chem., Sect. B., vol. 32B, No. 11, pp. 1178–1180.
Patra, A. et al, Chemical Abstracts, vol. 111, No. 9, Abstract 078441, Aug. 28, 1989.
Protiva, J. et al, Collection of Czechoslovak Chemical Communications, vol. 42, No. 4, 1977, pp. 1220–1228.
Protiva, J. et al, Collection of Czechoslovak Chemical Communications, vol. 41, No. 4, 1976, pp. 1200–1207.
Protiva, J. et al, Collection of Czechoslovak Chemical Communications, vol. 46, No. 11, 1981, pp. 2734–2741.
Akira Inada, et al., Chemical and Pharmaceutical Bulletin, Vo. 41, No. 3, Mar. 1, 1993, pp. 617–619.
Y. Noda, et al., Chemical and Pharmaceutical Bulletin, vol. 45, No. 10, Jan. 1, 1997, pp. 1665–1670.
Kim, D S H L, et al., Bioorganic & Medical Chemistry Letters, vol. 8, No. 13, Jul. 7, 1998, pp. 1707–1712.
Brenner, "Ovulation Inhibition with Nafarel in Acetate Nasal Administration for Six Months", Contraception, 1986.
Choi, Y., "Ellagic Acid Derivatives of Agrostistachys hookeri", Planta medica, 1988, pp. 511–513.
Inoue, H., "Inhibitory Effect of Glycyrrhetinic Acid Derivatives on Lipoxygenase and Prostaglandin Synthease", Chem. Pharm. Bull. vol. 34 (2), pp. 897–901, 1986.
Mosmann, T., "Rapid Colorimetric Assay for Cellular Growth and Survival: Application to Proliferation and Cytoxicity Assays" Journal of Immunlogical Methods, vol. 65., 1983, pp. 55–63.
Pisha, E., "Discovery of Betulinic Acid as a Selective Inhibitior of Human Melanoma that Functions by Induction of Apoptosis" Nature Medicine, vol. 1, No. 10, Oct. 1995, pp. 1046–1051.
Waller, D.P., "In Vitro Spermicidal Activity of gossypol", Contraception, Aug. 1980, vol. 22, No. 2, pp. 183–188.
Yasukawa, "Sterol and Triterpene Derivatives from Plants Inhibit the Effects of a Tumor Promoter, and Sitosterol and Betulinic Acid Inhibit Tumor Formation in Mouse Skin Two–Stage Carcinogenic", Oncology, 46:72–76, 1991.
Delporte, C.L., "Biological Activities and Metabolites from Trevoa Trinervis Miers", Phytotherapy Research, vol. 11, 504–507 (1997).

*Primary Examiner*—Jos'G. Dees
*Assistant Examiner*—Barbara Bado
*Attorney, Agent, or Firm*—Ladas & Parry

[57] ABSTRACT

The invention relates to use of betulinic acid and/or its derivatives for treating, inhibiting, and/or preventing tumors or cancer growth more particularly, to treating leukemia, lymphomas, lung, prostate and ovarian cancer. This invention also relates to novel betulinic acid derivatives and a composition containing betulinic acid derivatives with or without betulinic acid.

34 Claims, 4 Drawing Sheets

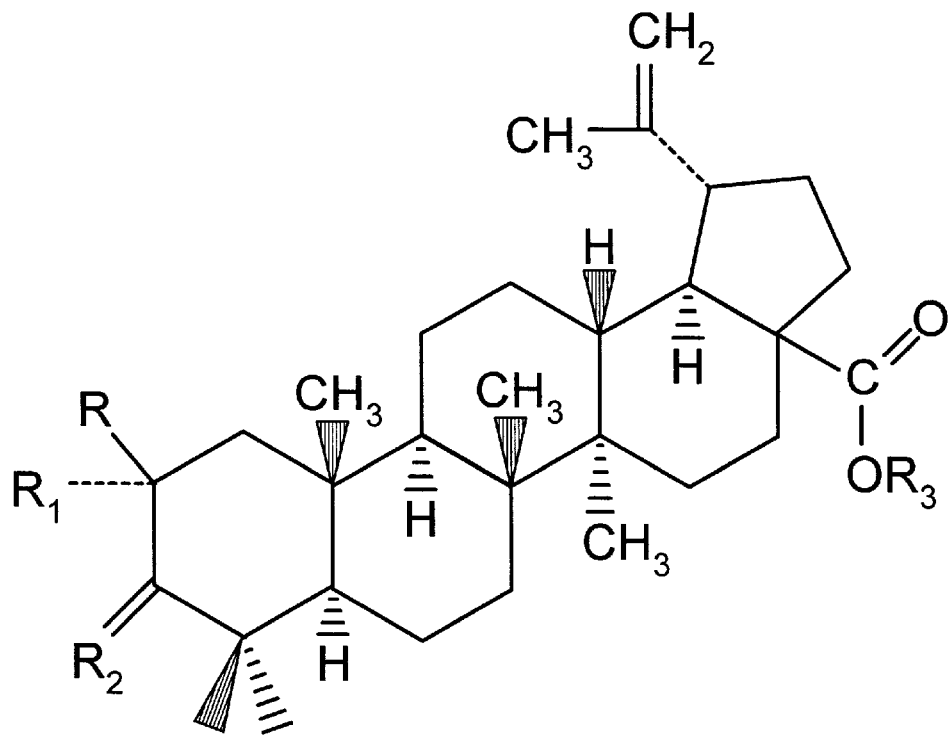
F I G. 5
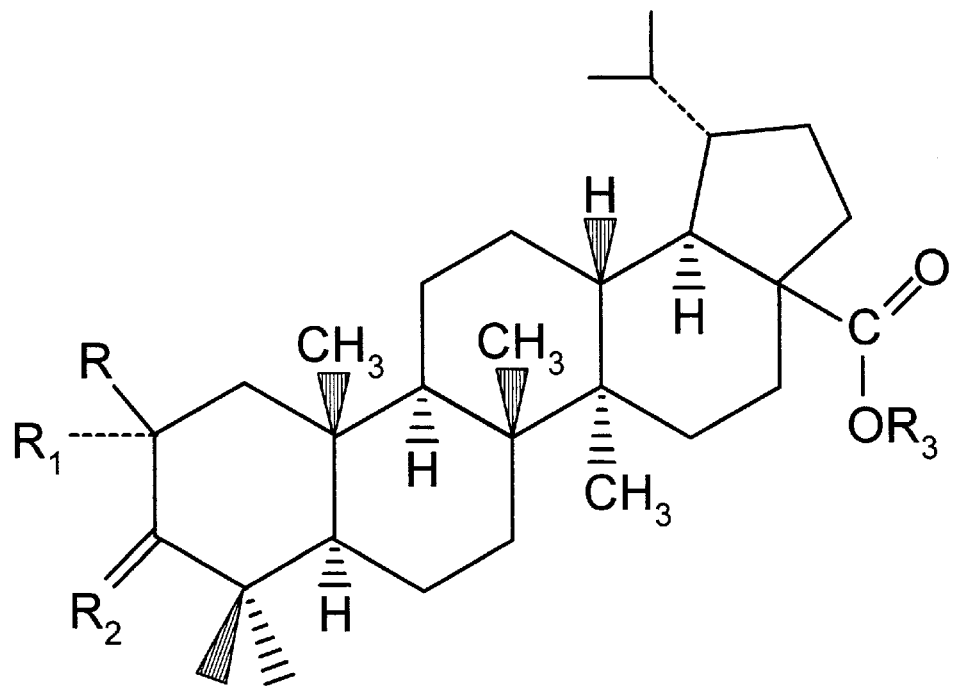
F I G. 6

USE OF BETULINIC ACID AND ITS DERIVATIVES FOR INHIBITING CANCER GROWTH AND A METHOD OF MONITORING THIS

FIELD OF THE INVENTION

The invention relates to use of betulinic acid and/or its derivatives for treating, inhibiting, and/or preventing tumors or cancer growth more particularly, to treating leukemia, lymphomas, lung, prostate and ovarian cancer. This invention also relates to novel betulinic acid derivatives and a composition containing betulinic acid derivatives with or without betulinic acid.

BACKGROUND OF THE INVENTION

Significant progress has been achieved in the management of adult acute leukemia. However, long term disease free survival is currently achieved in less than 50% of patients. Optimal therapy has not yet been defined and stratification of therapy according to prognostic factors is only now beginning to be addressed. Acute leukemia (AL) is an uncommon form of malignancy affecting approximately five persons per 100,000 in the U.S. annually with a 90% mortality rate within one year of diagnosis. Although incidence of leukemia over all has been stable for the last 30 years, the increasing age of the population will presumably result in a greater number of cases being reported.

On the other hand, malignant lymphomas are the seventh most common cause of death from cancer in the United States. In 1992, approximately 41,000 new cases were diagnosed, and there were approximately 19,400 deaths from the disease. The incidence of lymphocytic lymphomas is increasing each year; the 50% increase in incidence between 1973 and 1988 reported by the American Cancer Society was one of the largest increases reported for any cancer. A large portion of the increase has been attributed to the lymphocytic lymphomas developing in association with acquired immunodeficiency syndrome (AIDS).

In the treatment of acute myelogenous leukemia (AML) in adults corticosteroids, methotrexate, 6-mercaptopurine and vincristine were used, initially as single agents and subsequently in combination. The emergence of ara-C as the major single agent in the management of AML in the late 1960s converted this incurable disease to a potentially curable condition. The subsequent development of anthracyclines, such as daunorubicin, doxorubicin (Adriamycin), rubidazone and idarubicin allowed new combinations to be developed. The vinca alkaloids, alone or in combination with corticosteroids, and epidophyllotoxins, methotrexate, 6-mercaptopurine, cyclophosphamide and L-asparaginase have only minor activity against adult AML. Most regimens in adult AL incorporate vincristine, corticosteroids, prednisone or dexametlhasone, anthracyclines, and L-asparaginase.

The predominant treatments for AL have been in place for 5 to 15 years. No major class of drugs for the management of AL has been discovered. The allogenic and autologous marrow transplant program with monoclonal purging and chemotherapy purging have been applied with no major difference in response or survival rates.

The treatment approach to a particular patient with lymphocytic lymphoma is determined by the tumor histology, the stage of disease, and the physiologic status of the patient. The most active chemotherapy programs for intermediate-grade lymphomas include therapy using different combinations, dosages and schedules of cyclophosphamide, doxorubicin, vincristine, procarbazine, prednisone, bleomycin and methotrexate. Development of new drugs that are selective for particular subsets of leukemia and lymphoma patients is of the highest priority.

Second only to lung cancer as a cause of cancer deaths, prostate cancer has become the most common cancer among American men. It was predicted that 316,000 new cases of prostate cancer would be diagnosed in 1996, causing 40,000 deaths. Potential prostate cancer chemopreventive agents under consideration are diverse with respect to source, chemical structure and physiological effects. The candidate drugs under development for treatment of prostate cancer must demonstrate long-term safety and minimum toxicity after long term administration. Retinoids such as lycopene and 4-hydroxyphenretiminide and difluoromethyl ornithine (DFMO) are being evaluated in patients scheduled for radical prostatectomy. Androgen deprivation may also have a role in chemoprevention. Other approaches under study include the use of vitamin D analogs, $\alpha$-tocopherol and dietary restriction of fat. Conventional chemotherapeutic agents used for hormonally relapsed prostate cancer are doxorubicin, ketonazole, cyclophosphamide, prednisolone, estramustine, vinblastine, paclitaxel, mitoxantrone, either alone or in combination.

The vast majority of ovarian cancers are epithelial in origin and these account for more than 90% of the estimated 26,700 new cases of ovarian cancers that were diagnosed in the United States in 1996. Ovarian cancer is the leading cause of death from a gynecologic cancer. From 1970 to 1991, survival rates for patients with ovarian cancer have increased from 36% to 44%. This improvement in survival rate is in large part due to the development of curative platinum-based chemotherapy for patients. The generally accepted treatment for patients with either stage III or IV (advanced-stage) ovarian cancer has been similar: cytoreductive surgery when feasible, followed by chemotherapy. Chemotherapeutic agents from a wide variety of different classes have been shown to produce responses in patients with ovarian cancer. Before the demonstration of marked activity of paelitaxel in ovarian cancer, platinum compounds were considered to be the most active agents in this disease. Both paclitaxel and docetaxel have been demonstrated to have activity in platinum-resistant patients. Gemcitabine, a pyridine antimetabolite, has been shown in phase II trials in Europe to be an active agent.

Under the auspices of a National Cooperative Natural Product Drug Discovery Group supported by the National Cancer Institute, the potential antitumor activity of approximately 2500 extracts derived from globally collected plants was evaluated in a panel of enzyme based assays and in a battery of cultured human tumor cell lines. One such extract, prepared from the stem bark of *Ziziphus mauritiana* Lam. (Rhamnaceae), displayed selective cytotoxicity against cultured human melanoma cells (Nature Medicine, Pisha et al., Vol. 1, No. 10, pages 1046–1051, October 1995; WO 96/29068). As a result of bioactivity guided fractionation, betulinic acid, a pentacyclic triterpene, was identified as a mclanoma-speciflic cytotoxic agent. In follow-up studies conducted with athymic mice carrying human melanomas, tumor growth was completely inhibited without toxicity. As judged by a variety of cellular responses, antitumor activity was mediated by the induction of apoptosis. On page 1047 of Nature Medicine, Vol. 1 (10), 1995 it is stated that growth of human cancer cell types other than melanoma were recalcitrant to treatment with betulinic acid. It is also disclosed on page 1049 that although initial reports reported betulinic acid as active against the Walker 256 murine carcinosarcoma tumor system, L1210 murine lymphocytic leukemia model and P-388 murine lymphocyte test, these results were not reproduced in subsequent tests.

A number of triterpenoids, including betulinic acid, have several known medical applications including use as an anticancer drug. Anderson et al., in WO 95/04526, discuss derivatives of triterpenoids which have been used in cancer therapy, including their activity against polyamines which are required by cells to grow at an optimal rate. Some of these triterpenoids have been found to interfere with enzymatic synthesis of polyamines required for optimal cell growth, and thus inhibit the growth of cancer cells, particularly by inhibiting ornithine decarboxylase (Yasukawa, K. et al. Oncology 48 : 72–76, 1991). Thle anti-cancer activity of betulinic acid and some derivatives has been demonstrated using mouse sarcoma 180 cells implanted subcutaneously in nude mice (JP 87-301580). Choi et al have shown that betulinic acid 3-monoacetate, and betulinic acid methyl ester exhibit $ED_{50}$ values of 10.5 and 6.8 $\mu$g/ml, respectively, against P388 lymphocytic leukemia cells (Choi, Y-H et al., Planta Medica vol XLVII, pages 511–513, 1988). According to Choi, a compound is considered active in the P388 system if it has an $ED_{50}$ of $\leq 4.0$ $\mu$g/ml.

Betulinic acid has been reported also to possess anti-inflammatory activity. The anti-inflammatory activity of betulinic acid is, at least in part, due to its capacity to inhibit enzymes involved in leukotriene biosynthesis, including 5-lipoxygenase (Somatsu, S. et al., Skin and Urology 21: 138, 1959 and Inoue, H., et al., Chem Pharm Bull. 2: 897–901, 1986).

Betulinic acid and dihydrobetulinic acid acyl derivatives have been found to have potent anti-HIV activity (WO 96/39033). Anti-HIV assays indicated that 3-O-(3', 3'-diimethylsuccinyl)-betulinic acid and dihydrobetulinic acid both demonstrated extremely potent anti-HIV activity in acutely infected H9 lymphocytes with $EC_{50}$ values of less than $1.7 \times 10^{-5}$ $\mu$M, respectively.

Thus, betulinic acid and its derivatives have been shown to possess several medicinal properties including anticancer activity. But apart from the conclusive evidence of its anti-melanoma activity, it has not so far been shown to possess anticancer activity on other cancers. We report here for the first time anti-leukemia and anti-lymphoma activity of betulinic acid and its derivatives with $ED_{50}$ values in the range of approximately 0.5 to 4.0 $\mu$g/ml. Further we also report for the first time anti-prostate cancer activity of betulinic acid and its derivatives with $ED_{50}$ values in the range of approximately 0.6 to 6.8 $\mu$g/ml. Activity against lung cancer is also demonstrated. Betulinic acid derivatives have an $ED_{50}$ value in the range of 0.4 to 8.1 $\mu$g/ml against ovarian cancer.

SUMMARY OF THE INVENTION

The invention provides a method of treating a patient suffering from leukemia, lymphonma, prostate, lung or ovarian cancer by administering a pharmaceutically eflective dosage of betulinic acid and/or betulinic acid derivatives. This invention also provides for novel betulinic acid derivatives and compositions containing them with pharmaceutical acceptable additives, diluents, carriers, and excipients with or without betulinic acid.

Another object of the invention relates to providing novel betulinic acid derivatives which are used for treating cancer or tumors.

Another object of the invention is to provide a compound and compositions for treating, inhibiting and/or preventing tumor growth and particularly, for treating, inhibiting and/or preventing the growth of leukemia and lymphomas and for treating, inhibiting and/or preventing the growth of prostate, lung and ovarian cancers using a natural product-derived compound and its derivatives.

Another object of the invention is to provide a treatment method using betulinic acid and/or it derivatives to prevent the growth of cancerous cells, wherein betulinic acid or its derivatives is administered systemically.

Yet another object of the invention is to overcome the problem of high toxicity associated with standard chemotherapeutic agents by using a natural product-derived compound, e.g. betulinic acid or its derivatives.

Still another object of the invention is to overcome the problem of insufficient availability associated with synthetic anticancer agents by using readily available betulinic acid and its semisynthetic derivatives.

Another object of the invention is to overcome the problem of high costs of synthetic anticancer agents by utilizing the readily available natural product derived compound, e.g. betulinic acid and it derivatives which is expected to be less expensive than other chemotherapeutic drugs.

These and other objects of the present invention will become apparent from the description of the invention disclosed below, which descriptions are intended to limit neither the spirit or scope of the invention but are only offered as illustrations of the preferred embodiments of the invention.

BRIEF DESCRIPTION OF THE FIGURES

FIG. 5 is a formula representing certain betulinic acid derivatives.

FIG. 6 is a formula representing certain betulinic acid derivatives.

DETAILED DESCRIPTION OF THE INVENTION

The present invention provides a pharmaceutical compound useful for killing, inhibiting and/or preventing multiplication of cancer cells. The invention provides a method for treatment of humans, mammals, or other animals suffering from cancer or other tumors. The method comprises administering a therapeutically effective dose of betulinic acid and/or betulinic acid derivatives either alone or in a pharmaceutical composition containing the compounds so as to kill, inhibit or prevent the multiplication of cancer or tumor cells. In a preferred embodiment, pharmaceutically acceptable carriers, diluents, excipients and/or solvents are used with betulinic acid and/or its derivatives. The method of treatment of the present invention may be particularly useful in the treatment of leukemia and lymphomas, and in the treatment of prostate, lung and ovarian cancer.

Betulinic acid is isolated by methods known in the art comprising the steps of preparing an extract from the bark of

*Ziziphus jujuba* Mill. (Rhamnaceae), or *Ziziphus mauritiana* Lam (Rhamnaceae). Betulin can be isolated from white-barked birch trees (Betula spp.) and converted to betulinic acid (Pisha, E. et al, Nature Medicine, Vol. 1, No. 10, October 1995, p. 1046–1051). From use of a panel of human tumor cell lines it was shown that betulinic acid and novel derivatives of betulinic acid prepared directly or indirectly from betulinic acid mediated a selective cytotoxic profile against human leukemias, lymphomas, prostate, lung and ovarian cancer. The bioactivity of derivatives of betulinic acid were tested using cultured human leukemia (MOLT-4, Jurkat E6.1, CEM.CM3), lymphoma cells (BRISTOL-8, U937), prostate cancer cells (DU 145), lung cancer cells (L132 and A549) and ovarian cancer cells (PA-1) as the monitors.

Figure 1:
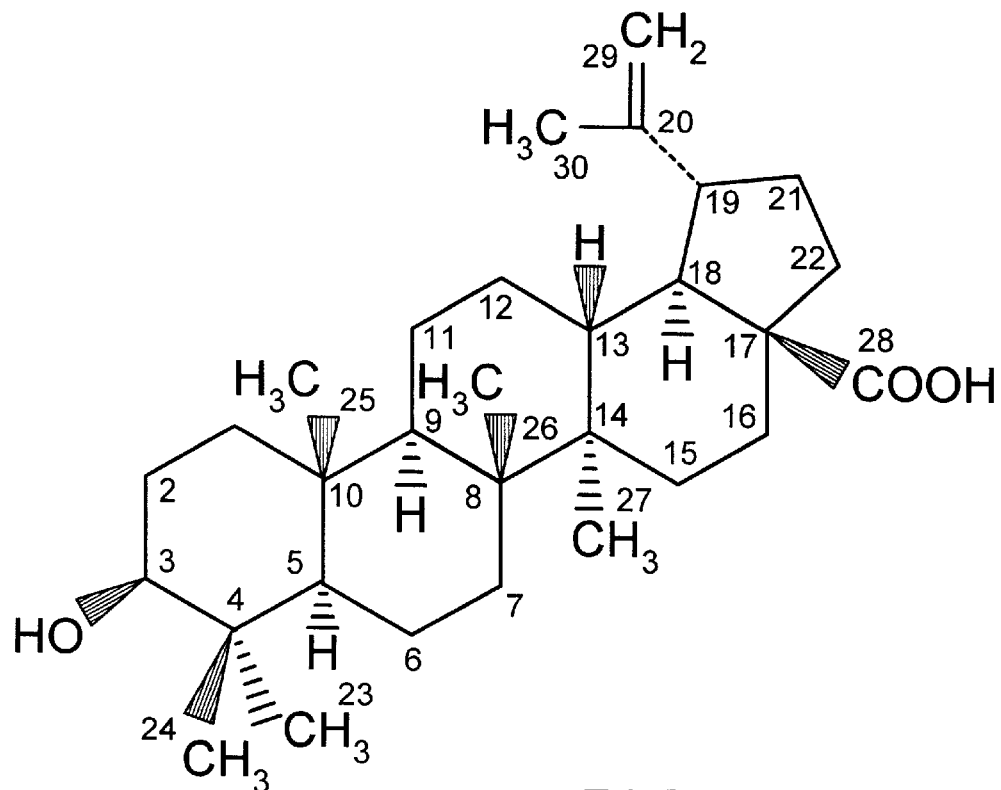
FIG. 1 is the formula representing betulinic acid.
Figure 2:
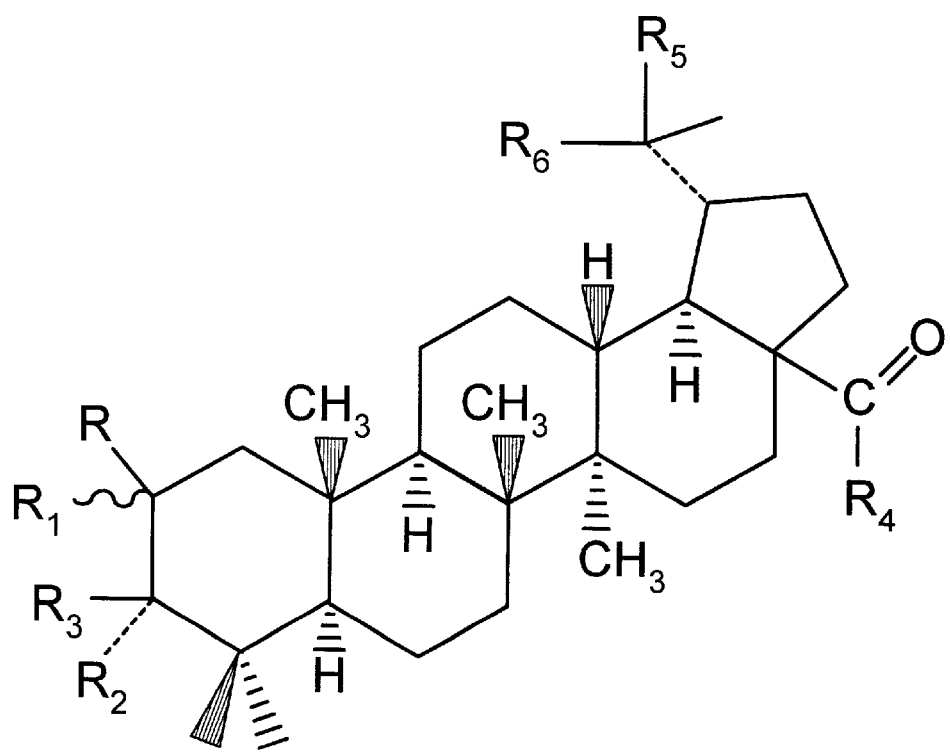
FIG. 2 is a formula representing certain betulinic acid derivatives.

The present invention also comprises novel betulinic acid derivatives used for killing, inhibiting and/or preventing multiplication of cancer or tumor cells. The derivatives of betulinic acid have a basic skeleton of betulinic acid as shown in FIG. 2 of the accompanying drawings,

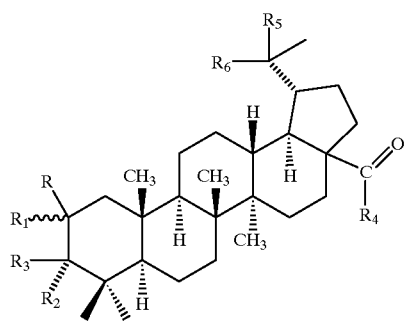

2 wherein R, $R_1$, $R_2$, $R_3$, $R_4$, $R_5$ and $R_6$ independently or in combination represent the following groups:

R is H;

$R_1$ is H, Br, Cl, F or I;

$R_2$ is H and $R_3$ is OH, $OCOCH_3$, $OCO(CH_2)_nCH_3$ (where n=1 to 5), $OCOC(CH_3)_3$, $OCO(CH_2)_n Cl$ (where n=1 to 10), $OCOC_6H_5$, $NH_2$, $OCOC_6H_2Cl_3$, $OCOCH(OCOCH_3)CH_3$, $OCOCH(OCOCH_3)C_6H_5$, $OCOCH_2C_6H_5$ or

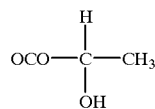

$R_2$ and $R_3$ together are O, $NNHC_6H_5$, $NNHC_6H_2Cl_3$, $NNHC_6H_4OCH_3$, $NNHC_6H_4OH$, $NNHC_6H_3(Br)(OCH_3)$ or N—OX (X being H, $COCH_3$, $SO_2C_6H_4CH_3$, or $CO(CH_2)_nCH_3$ (where n=1 to 5));

$R_4$ is OH, —$OCH_3$, $O(CH_2)_nCOOCH_3$, $O(CH_2)_n COOC_2H_5$, $O(CH_2)_nCOOH$, $O(CH_2)_nCOCl$ (where n=1 to 5), $OCH_2CH_2OC_2H_5$, $OCH_2CH_2OH$, $OCH_2CH_2OCOCH_3Cl$, $N_3$, $NHNH_2$, $HNNHC_6H_4OMe$, $NHNHC_6H_2Cl_3$, $NH_2$ or $NH(CH_2)_n CH_3$ (where n=0 to 9); $R_5$ is H or Br;

$R_6$ is $CH_3$, $CH_2Br$, $CH_2OH$, CHO, $CH_2OCOCH_3$, COOH, $COO(CH_2)_nCOOCH_3$, $COO(CH_2)_nCOOC_2H_5$, $COO(CH_2)_n COOH$ (where n=1 to 5); or $R_5$ and $R_6$ together are >C=$CH_2$, or >CH—$CH_3$.

When $R_2$ and $R_3$ together are O, this represents a carbonyl group.

Figure 3:
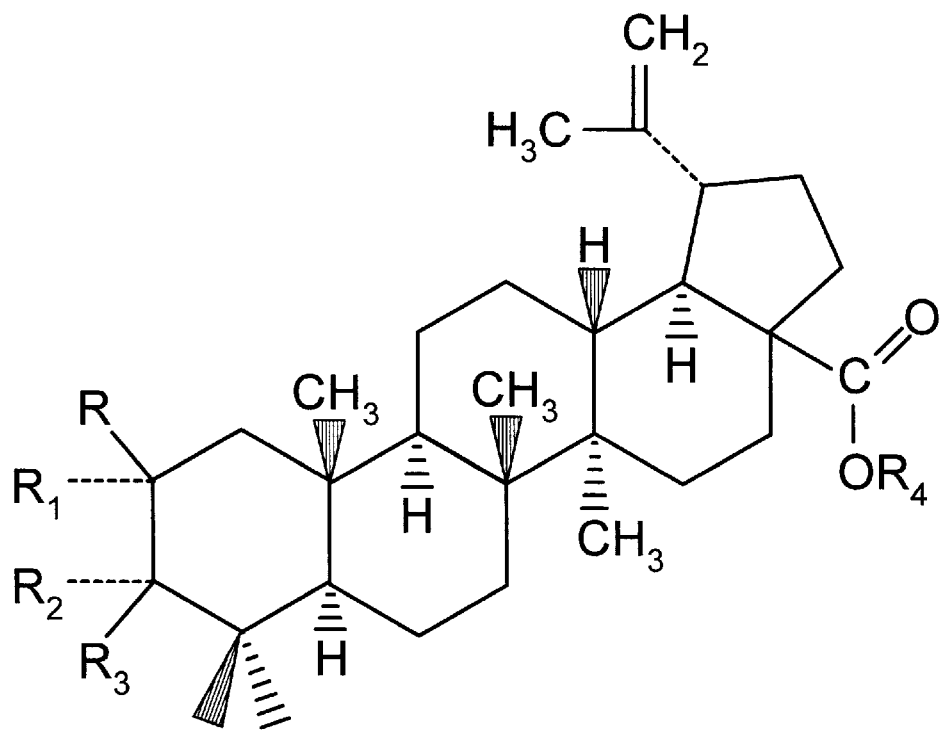
FIG. 3 is a formula representing certain betulinic acid derivatives.

The preferred novel compounds of the invention are shown in FIGS. 3 to 8 of the accompanying drawings in which the meanings of $R_1$, $R_2$, $R_3$, $R_4$, $R_5$ and $R_6$ are given below:

Compounds of FIG. 3 of the drawings: R=H; $R_1$=H; $R_2$=H; $R_3$=$OCOCH(OCOCH_3)CH_3$, OH, $OCOCH_3$, $OCOCH_2CH_3$, $OCOC_6H_5$, $NH_2$, $OCOCH(OCOCH_3)C_6H_5$, or $OCOC(CH_3)_3$ and $R_4$=H, $CH_2COOCH_3$ or $CH_2COOH$.

Figure 4:
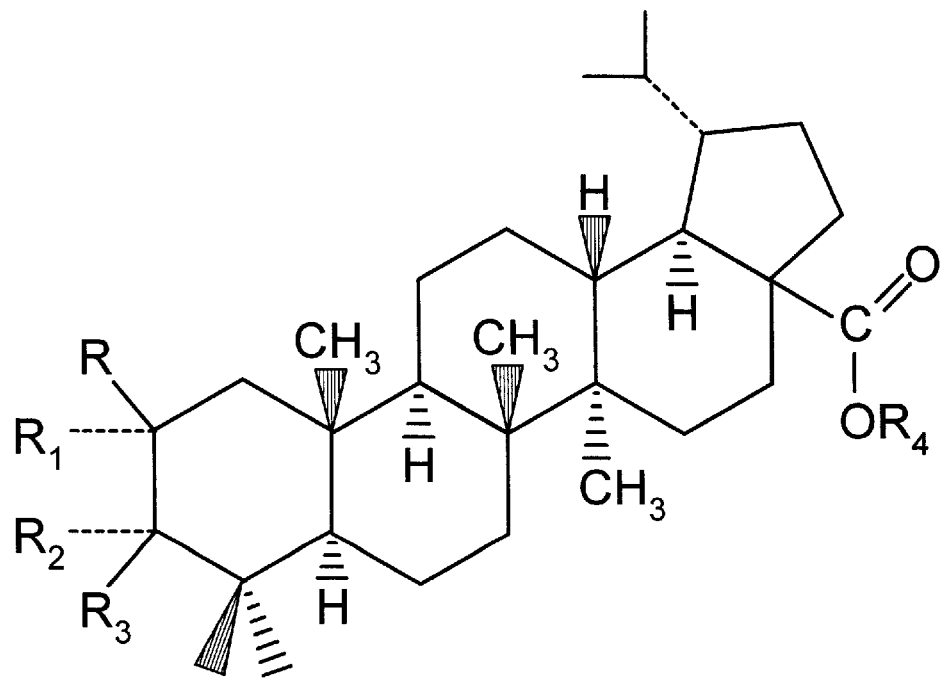
FIG. 4 is a formula representing certain betulinic acid derivatives.

Compounds of FIG. 4 of the drawings: R=H; $R_1$=H; $R_2$=H; $R_3$=$OCOCH(OCOCH_3)CH_3$, $OCOCH_3$, $OCOC_6H_5$ or OH and $R_4$=H, $CH_2COOH$ or $CH_2COOCH_3$.

Compounds of FIG. 5 of the drawings: R=H; $R_1$=H; $R_2$=O, N—OH, N—NH—Ph, N—O—$SO_2$—$C_6H_4CH_3$, $NNHC_6H_4OCH_3$ or N—$OCOCH_3$; and $R_3$=H or $CH_2COOCH_3$.

Compounds of FIG. 6 of the drawings: R=H; $R_1$=H; $R_2$=NOH, $NNHC_6H_2Cl_3$, $NNHC_6H_4OCH_3$, $NNHC_6H_3(Br)(OCH_3)$ or $NNHC_6H_5$; and $R_3$=H.

Figure 7:
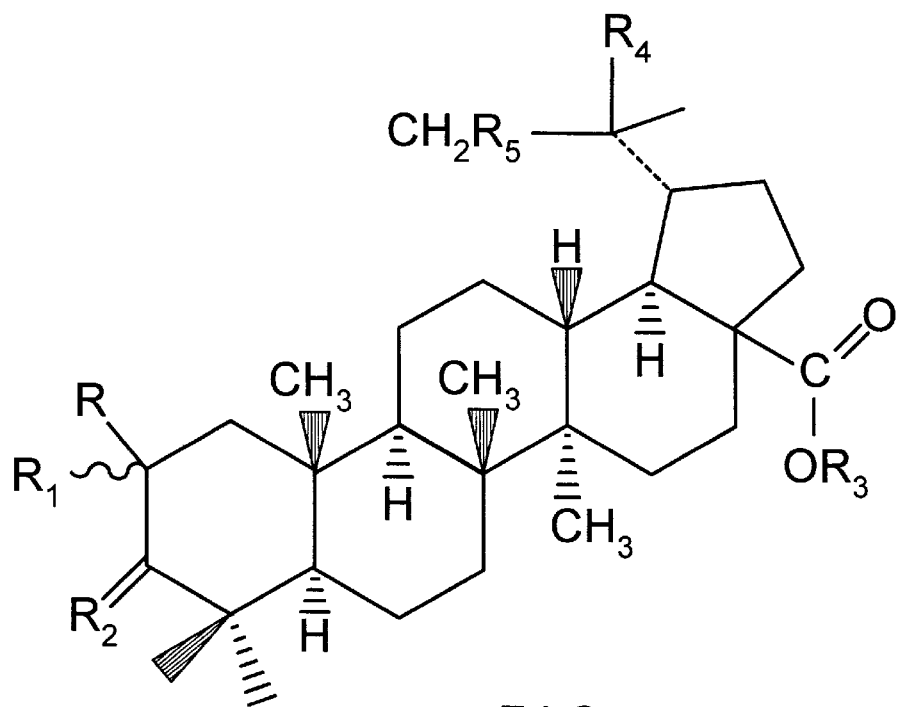
FIG. 7 is a formula representing certain betulinic acid derivatives.

Compounds of FIG. 7 of the drawings: R=H; $R_1$=Br; $R_2$=O or $NNHC_6H_3(Br)(OCH_3)$; $R_3$=H, $CH_2COOCH_3$ or $CH_2CH_2COOCH_3$; $R_4$=H or Br, and $R_5$=H or Br.

Figure 8:
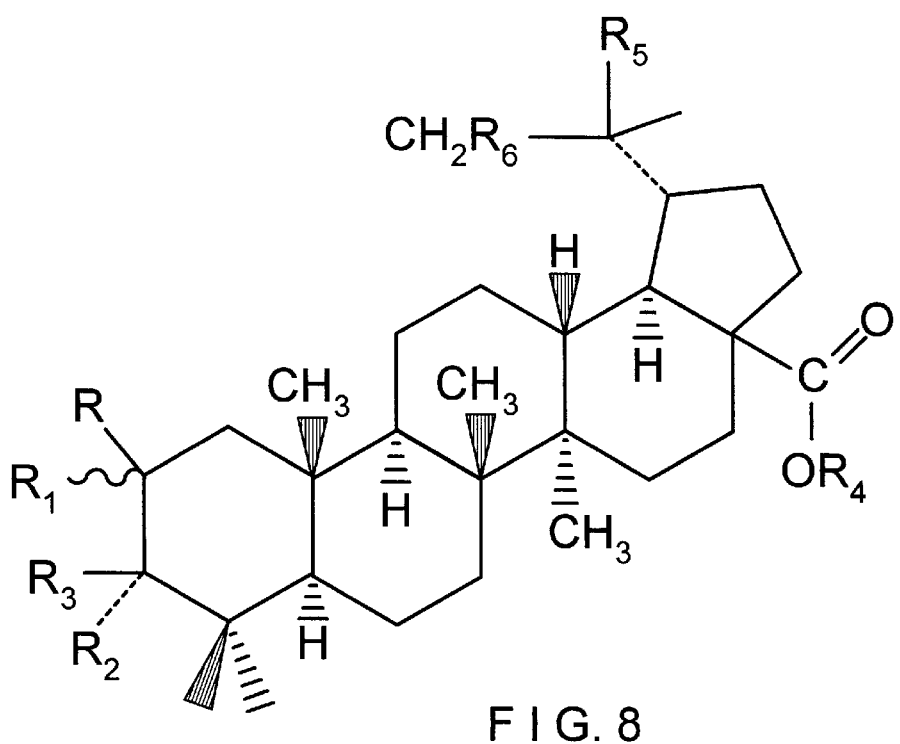
FIG. 8 is a formula representing certain betulinic acid derivatives.

Compounds of FIG. 8 of the drawings: R=H; $R_1$=H or Br; $R_2$=H; $R_3$=$OCOCH_3$ or OH; $R_4$=H, $CH_2COOCH_3$ or $CH_2COOH$; $R_5$=H or Br; and $R_6$=H or Br.

The invention also relates to methods of preparing the novel compounds and in the examples below the term "substrate" refers to either betulinic acid, dihydrobetulinic acid or their derivatives as starting material unless otherwise indicated. Dihydrobetulinic acid is obtained from betulinic acid by reduction of $C_{20-29}$ double bond, whereas dihydrobetulinic acid derivatives refers to its derivitisation at either $C_3$ and/or $C_{17}$ positions. Conventional procedures known to those skilled in the art can be used in the preparation of the various betulinic acid derivatives wherein the starting material is betulinic acid or a derivative thereof unless otherwise specifically mentioned. The procedures mentioned below are either used alone or in combination to produce the novel derivatives.

The usual work-up used in the examples refers to evaporation of the reaction mixture, addition of water, extraction with organic solvent, washing and drying over an anhydrous compound, preferably anhydrous sodium sulfate and evaporation of organic layer.

EXAMPLE 1

Dried bark of *Ziziphus jujuba* Mill. (Rhamnaceae) was extracted with a hydrocarbon solvent at a temperature of approximately 40° to 120° C. (preferably 60° to 80° C.) for a period of approximately 24 hours. Examples of hydrocarbon solvents that can be used for the extraction are benzene, toluene and xylene. The combined extract was concentrated under vacuum to 1/20th to 1/100th (preferably 1/30th to 1/50th) of its original volume and chilled to 0–10° C. (preferably 0–5° C.) for 6 to 24 hours (preferably 12 to 16 hours). The crude betulinic acid thus obtained was separated by filtration. It was purified by either crystallization and/or by derivatization followed by de-derivatization. Purified Betulinic acid was characterized by comparing it with an authentic sample of betulinic acid with respect to melting point, mixed melting point, IR, UV & NMR spectra.

Preparation of Betulinic Acid Derivatives

The following procedures are either used alone or in combination to produce the derivatives of the present invention. In Examples 2, 3 and 7 the substrate used is betulinic acid, dihyrobetulinic acid or their derivatives.

EXAMPLE 2
Preparation of 3-o-acyl Derivatives

Method I: Substrate in organic base is treated with suitable anhydride at room temperature for approximately 4–16 hours. Examples of anhydrides that can be used in this process are represented by general formula $(RCH_2CO)_2O$ wherein R=H, $CH_3$, $C_2H_5$, etc. The reaction was worked up by evaporation of the reaction mixture, addition of water and extraction with an organic solvent. The organic layer was dried over anhydrous sodium sulfate, evaporated and residue crystallized to yield the corresponding pure 3-o-acyl derivatives respectively. Examples of organic bases that can be used in this method are TEA, pyrdine and DMAP.

Method II: Substrate in halogenated organic solvent was treated with suitable acyl chloride as in Method I. The reaction was worked up as described in Method I to yield the corresponding 3-o-acyl derivatives in the pure form. Examples of acyl chlorides that can be used are $RCH_2(CH_2)_nCOCl$ wherein R=H, Cl or Br and n=0 to 9 or $RCH_2(CH)_nXCOCl$ wherein R=H, X=OH or $OCOCH_3$ and n=1. The halogenated solvent may be selected from $CCl_4$, $CH_2Cl_2$ or the like.

EXAMPLE 3
Preparation of 3-oxo Derivatives

The substrate was dissolved in an organic solvent and conventional oxidizing agent was added under normal reaction conditions. The reaction was worked up as described in Method I to yield the corresponding 3-oxo derivatives in the pure form.

Examples of oxidizing agents that can be used are $CrO_3$/Py; $CrO_3/H_2SO_4$; $CrO_3/AcOH$ or the like. Normal reaction condition is stirring the substrate with oxidizing agent at from 0° C. to room temperature for a few hours. The organic solvent may be selected from acetone, $CH_2Cl_2$, AcOH, mixtures thereof or the like.

EXAMPLE 4
Preparation of 2, 20, 29-tribromo 3-oxo Derivative

A 3-oxo betulinic acid derivative prepared according to the process of Example 3 was dissolved in halogenated organic solvent. To this was added dropwise liquid bromine dissolved in the same solvent and the temperature was maintained between 0–10° C. The reaction mixture was brought to room temperature and stirred for a few hours. The reaction was worked up as described in Method I of Example 2. The organic layer was washed with 5–10% aqueous alkaline solution and evaporated. The crystallized product yielded pure 2, 20, 29-tribromo-3-oxo derivatives. Examples of halogenated solvents that can be used are $CCl_4$, $CH_2Cl_2$, $CHCl_3$ and the like. Examples of aqueous alkaline solution that can be used are bicarbonate or carbonate of an alkali metal in water, and the like.

3-Oxo-derivatives of betulinic acid, dihydrobetulinic acid or their derivatives can be used in the processes of Examples 5 and 6.

EXAMPLE 5
Preparation of 3-oximino Derivative

A 3-oxo derivative is mixed in an alcoholic solvent such as methanol, ethanol, propanol and the like. To this was added hydroxylamine, phenyl hydroxylamine or benzyl hydroxylamine or a salt thereof; and sodium acetate. The mixture was refluxed for a few hours. The reaction mixture was evaporated to dryness. The reaction was worked up as described in Method I of Example 2 and yielded crude-3-oximino derivative which crystallized to yield the corresponding pure 3-oximino derivative.

EXAMPLE 6
Preparation of Phenylhydrazone of 3-oxo Derivative

Phenylhydrazine or its phenyl substituted analogs or a salt thereof, and sodium acetate were added to 3-oxo derivative dissolved in alcoholic solvent such as methanol, ethanol, propanol and the like, and was refluxed for about four hours. The reaction was worked up as described in Method I of Example 2 to yield the corresponding pure phenylhydrazone derivative in pure form.

EXAMPLE 7
Preparation of 17 and/or 20-Carboxyalkyl Carboxylate

To the substrate dissolved in dry dimethylformamide, sodium hydride was added and the mixture was stirred at room temperature for about two hours. A suitable haloalkyl carboxyester was added to the above reaction mixtures and the mixture was stirred at room temperature for I 6–20 hours. The reaction was worked up as described in Method hours. I of Example 2 to yield pure 17 and/or 20-carboxyalkyl carboxylate derivative. Examples of haloalkyl carboxy esters that can be used are chloro or bromo derivative of methyl or ethyl acetate, or chloro or bromo derivative of propionate and the like.

EXAMPLE 8
Preparation of 17 and/or 20-Carboxyalkyl Carboxylic Acid 17 and/or 20-carboxyalkyl carboxylate was dissolved in an alcoholic solvent such as methanol, ethanol, propanol or the like to which a hydroxide such as sodium or potassium hydroxide or the like was added. The mixture was warmed to 40–50° C. for 2–4 hours. The reaction was worked up as described in Method I of Example 2 to yield pure 17 or 20-carboxyalkyl carboxylic acid derivative.

EXAMPLE 9
Preparation of 2-bromo-3-oxo-Derivative:

3-oxo-dihydrobetulinic acid derivative was dissolved in halogenated organic solvent such as $CCl_4$, $CH_2$, $Cl_2$, $CHCl_3$ or the like. Liquid bromine dissolved in the same solvent was added dropwise while maintaining the temperature between 0–10° C. The reaction mixture was brought to room temperature and maintained for a few hours. The mixture was worked up in the usual manner, the organic layer was washed with 5–10% aqueous alkaline solution followed by water. Evaporation and crystallization yielded pure 2-Bromo-3-oxo derivatives. Examples of aqueous alkaline solution that can be used are bicarbonate or carbonate of an alkali metal in water, and the like.

EXAMPLE 10
Preparation of N—O-Tosyl or N—O-Acyl of 3-Oximino Derivative:

3-Oximino derivative is dissolved in dry DMF, sodium hydride is added and the reaction mixture is stirred at room temperature for a few hours. The mixture is cooled to 0–5° C. and suitable tosyl chloride or acyl chloride is added and stirring is continued at this temperature for a few hours. The usual work up gave the corresponding N-acyl or N—O-tosyl derivative. Acyl chloride that can be used is $R(CH_2)_nCOCl$ wherein R=H and n=1 to 5.

EXAMPLE 11
Preparation of 20, 29-dibromo Derivative:

Betulinic acid or its derivative (except 3-oxo-betulinic acid or its derivatives) was dissolved in halogenated organic solvent. To this liquid bromine dissolved in the same solvent was added dropwise and temperature maintained between 0–10° C. The reaction mixture was brought to room temperature and stirred for few hours. The reaction mixture was worked up as described in Method I of Example 2. The organic layer was washed in 5–10% aqueous alkaline solution and evaporated. The crystallized product yielded pure 20, 29-dibromo derivative. Examples of halogenated solvents that can be used are $CCl_4$, $CH_2Cl_2$, $CHCl_3$ and the like.

EXAMPLE 12
Preparation of 3-amino Derivatives:

3-oximino derivative is dissolved in glacial acetic acid and shaken under hydrogen atomosphere (60–70 psi) in presence of platinum oxide catalyst for several hours. Reaction mixture is filtered, mother liquor evaporated under vaccum to remove glacial acetic acid and the residue worked up in the usual manner to yield the corresponding 3-amino derivative.

EXAMPLE 13

In vitro cytotoxic activity of betulinic acid and its derivatives was determined by performing the MTT cytotoxicity assay (Mosmann T., J Immunological Methods, 65:55; 1983). Briefly, the cultured tumor cells were separately seeded in a 96-well culture plate and co-incubated with betulinic acid or its derivatives dissolved in methanol, dimethyl formamide, dimethyl sulfoxide or isopropyl alcohol with relevant controls at 37° C. in a $CO_2$ incubator. After 72 hours, the assay was terminated and percent cyotoxicities calculated. As shown in Table I, metabolic activity of leukemia cells (MOLT-4, Jurkat E6.1, HL60, CEM.CM3) was inibited by betulinic acid, i.e., an $ED_{50}$ value of about 0.6–3.0 μg/ml. Ihe $ED_{50}$ value of betulinic acid for lymphoma cells (BRISTOL-8, U937) was in the range of 0.5 to 1.0 μg/ml. Betulinic acid showed an $ED_{50}$ value of 1.30±0.55, 1.13±0.35 μg/ml and 2.20±0.70 μg/ml against L132 (human lung), DU145 (human prostate) and Malme 3M (human melanoma) respectively. The anticancer activity of betulinic acid on human lung and human prostate cancer has not been reported previously. None of the other cancer cell lines tested was affected by betulinic acid (i.e., $ED_{50}$ values of greater than 10 μg/ml). Table I includes data for betulinic acid only:

TABLE I

| S. No | Cell line | $ED_{50}$ (μg/ml) |
|---|---|---|
| 1 | HL 60 (Human myelogenous leukemia) | 2.80 ± 0.32 |
| 2 | K 562 (Human myelogenous leukemia) | 3.25 ± 0.49 |
| 3 | MOLT-4 (Human lymphoblastic leukemia) | 1.23 ± 0.70 |
| 4 | Jurkat E6.1 (Human lymphoblastic leukemia) | 0.65 ± 0.04 |
| 5 | CEM.CM3 (Human lymphoblastic leukemia) | 0.98 ± 0.03 |
| 6 | U937 (Human histiocytic lymphoma) | 0.69 ± 0.01 |
| 7 | BRISTOL-8 (Human B-cell lymphoma) | 0.84 ± 0.05 |
| 8 | MiaPaCa2 (Human pancreas) | >10 |
| 9 | HeLa (Human cervical) | >10 |
| 10 | PA-1 (Human ovary) | >10 |
| 11 | U87MG (Human glioblastoma) | >10 |
| 12 | U373MG (Glioblastoma) | >10 |
| 13 | MDA.MB.453 (Breast) | >10 |
| 14 | HT29 (Colon) | >10 |
| 15 | SW 620 (colon) | >10 |
| 16 | CoLo 205 (colon) | >10 |
| 17 | A549 (lung) | >10 |
| 18 | L132 (lung) | 1.30 ± 0.55 |
| 19 | KB (Oral) | >10 |
| 20 | DU145 (Prostate) | 1.13 ± 0.35 |
| 21 | Malme 3M (Melanoma) | 2.20 ± 0.70 |
| 22 | RPMI 8226 (Myeloma) | >10 |

EXAMPLE 14

Several derivatives of betulinic acid were prepared and characterized on the basis of spectral data. All the derivatives were screened for anti-leukemia activity using MOLT-4 as the monitor. Twenty-seven of these derivatives were screened for anti-leukemia, anti-lymphoma, anti-prostate cancer and anti-ovarian cancer activity using Jurkat E6.1, and CEM.CM3 (leukemia), U937 and BRISTOL 8 (lymphoma), DU145 (prostate); L132 and A549 (lung), and PA-1 (ovary) cell lines respectively. The results are given in Table II.

| | | Cell line | | | | | | | |
|---|---|---|---|---|---|---|---|---|---|
| S. No | DERIVATIVE | MOLT-4 | JurkatE6.1 | CEM.CM3 | BRISTOL8 | U937 | DU145 | PA-1 | A549 | L132 |
| 1 | MJ321-RS | 3.1 ± 0.2 | 1.8 ± 0.4 | — | 4.8 ± 1.2 | 1.6 ± 0.3 | 2.6 ± 0.5 | 4.1 ± 0.9 | >10.0 | >10.0 |
| 2 | MJ347-RS | 1.2 ± 0.1 | 0.4 ± 0.3 | 4.4 ± 0.2 | 2.6 ± 0.1 | 2.8 ± 0.6 | 3.1 ± 1.3 | 1.2 ± 0.4 | >10.0 | >10.0 |
| 3 | MJ351-RS | 3.4 ± 0.7 | 1.9 ± 1.6 | 3.7 ± 0.4 | 5.1 ± 1.7 | 2.0 ± 1.1 | 2.8 ± 1.2 | 8.1 ± 0.1 | >10.0 | 7.3 ± 3.0 |
| 4 | MJ352-RS | 5.9 ± 1.6 | 2.1 ± 0.5 | 2.8 ± 1.6 | 3.8 ± 3.3 | 2.1 ± 0.2 | 3.6 ± 1.8 | 5.1 ± 2.5 | >10.0 | >10.0 |
| 5 | MJ353-RS | 3.4 ± 0.7 | 2.6 ± 0.6 | 3.1 ± 0.1 | 3.4 ± 1.3 | 2.4 ± 1.3 | 2.4 ± 0.8 | 5.3 ± 0.3 | >10.0 | 4.3 ± 1.4 |
| 6 | MJ398-RS | 1.2 ± 0.4 | 0.9 ± 0.1 | 1.6 ± 0.5 | 1.7 ± 0.3 | 1.1 ± 0.1 | 1.6 ± 0.7 | 3.6 ± 0.1 | >10.0 | >10.0 |
| 7 | MJ408-RS | 4.0 ± 2.2 | 1.4 ± 0.1 | 3.2 ± 0.1 | 5.3 ± 0.5 | >10.0 | >10.0 | 5.9 ± 1.6 | >10.0 | >10.0 |
| 8 | MJ417-RS | 2.9 ± 0.6 | 3.1 ± 0.4 | 5.9 ± 0.3 | 7.4 ± 0.5 | 5.4 ± 0.1 | 1.9 ± 0.1 | 3.1 ± 0.1 | >10.0 | >10.0 |
| 9 | MJ434-RS | 2.4 ± 0.6 | >10.0 | >10.0 | >10.0 | >10.0 | 1.0 ± 0.1 | 0.7 ± 0.0 | >10.0 | >10.0 |
| 10 | MJ438-RS | 1.7 ± 1.0 | 0.5 ± 0.3 | 1.4 ± 0.1 | 1.4 ± 0.7 | 1.7 ± 0.3 | 5.5 ± 0.8 | 6.5 ± 0.0 | >10.0 | >10.0 |
| 11 | MJ443-RS | 3.1 ± 0.0 | >10.0 | >10.0 | 6.1 ± 0.0 | >10.0 | >10.0 | 1.3 ± 1.2 | >10.0 | >10.0 |
| 12 | MJ455-RS | 1.1 ± 0.9 | 1.6 ± 0.1 | 1.0 ± 0.1 | 3.4 ± 0.1 | 1.8 ± 0.1 | 0.9 ± 0.3 | 0.8 ± 0.1 | 2.3 ± 0.7 | 2.9 ± 0.7 |
| 13 | MJ457-RS | 3.9 ± 0.0 | 7.4 ± 0.7 | 6.4 ± 0.4 | 4.5 ± 0.6 | >10.0 | 2.9 ± 0.1 | 7.1 ± 1.2 | >10.0 | >10.0 |
| 14 | MJ458-RS | 0.6 ± 0.4 | 4.9 ± 3.9 | 1.3 ± 0.1 | 4.4 ± 0.3 | 0.9 ± 0.1 | 0.7 ± 0.1 | 0.7 ± 0.1 | 2.2 ± 0.2 | 2.4 ± 0.1 |
| 15 | MJ462-RS | 2.8 ± 0.0 | 3.8 ± 0.1 | 3.1 ± 0.0 | 2.1 ± 0.2 | 4.0 ± 0.3 | 1.0 ± 0.3 | 1.3 ± 0.1 | 2.1 ± 0.9 | 7.7 ± 2.1 |
| 16 | MJ463-RS | 2.1 ± 0.2 | 1.8 ± 0.0 | 2.6 ± 0.1 | 1.6 ± 0.1 | 2.4 ± 0.3 | 1.1 ± 0.4 | 0.7 ± 0.1 | 1.8 ± 0.3 | 1.5 ± 0.6 |
| 17 | MJ481-RS | 2.2 ± 0.7 | 2.9 ± 0.1 | 4.2 ± 0.1 | 3.4 ± 0.1 | 5.5 ± 0.8 | 2.9 ± 2.5 | 3.7 ± 2.5 | >10.0 | 5.3 ± 2.5 |
| 18 | MJ484-RS | 2.7 ± 0.2 | 4.9 ± 0.4 | 1.5 ± 0.1 | 3.3 ± 0.4 | 4.8 ± 0.4 | 2.8 ± 0.1 | 1.8 ± 1.2 | >10.0 | >10.0 |
| 19 | MJ487-RS | 1.4 ± 0.0 | 6.3 ± 0.0 | 2.9 ± 0.6 | 3.7 ± 0.1 | 2.2 ± 1.1 | 0.6 ± 0.1 | 0.4 ± 0.0 | >10.0 | 7.4 ± 2.9 |
| 20 | MJ524-RS | 1.3 ± 0.0 | 1.1 ± 0.2 | 1.2 ± 0.1 | 1.9 ± 0.3 | 0.7 ± 0.1 | 4.5 ± 2.3 | 2.5 ± 0.7 | >10.0 | >10.0 |
| 21 | MJ525-RS | 2.8 ± 0.8 | 5.5 ± 1.7 | 2.5 ± 0.1 | 3.4 ± 2.0 | >10.0 | >10.0 | 0.5 ± 0.1 | >10.0 | >10.0 |
| 22 | MJ527-RS | 1.7 ± 0.4 | 2.8 ± 0.0 | 2.1 ± 0.1 | 3.4 ± 0.1 | 1.1 ± 0.1 | 6.8 ± 1.3 | 3.2 ± 0.1 | >10.0 | >10.0 |
| 23 | MJ529-RS | 3.3 ± 0.7 | 2.1 ± 0.6 | 5.5 ± 0.1 | 2.1 ± 0.2 | 6.8 ± 0.5 | 4.2 ± 0.8 | 3.7 ± 0.8 | >10.0 | >10.0 |
| 24 | MJ542-RS | 0.4 ± 0.1 | 0.7 ± 0.2 | 0.3 ± 0.1 | 2.9 ± 0.1 | 1.3 ± 0.8 | 3.0 ± 0.1 | 0.5 ± 0.0 | >10.0 | >10.0 |

-continued

| S. No | DERIVATIVE | MOLT-4 | JurkatE6.1 | CEM.CM3 | BRISTOL8 | U937 | DU145 | PA-1 | A549 | L132 |
|---|---|---|---|---|---|---|---|---|---|---|
| 25 | MJ544B-RS | 3.6 ± 0.0 | >10.0 | 6.8 ± 0.1 | 7.0 ± 0.1 | >10.0 | >10.0 | 6.0 ± 2.7 | >10.0 | >10.0 |
| 26 | MJ548-RS | 1.2 ± 0.0 | 1.9 ± 0.3 | 1.9 ± 0.1 | 2.3 ± 0.2 | 1.2 ± 0.1 | 6.6 ± 3.1 | 4.8 ± 1.9 | >10.0 | >10.0 |
| 27 | MJ549-RS | 2.8 ± 0.0 | 6.9 ± 1.7 | 2.7 ± 0.1 | 1.4 ± 0.2 | 0.3 ± 0.0 | 2.5 ± 1.6 | 2.4 ± 2.4 | >10.0 | >10.0 |

EXAMPLE 15

Several derivatives of betulinic acid were prepared by making substitutions and/or structural changes at $C_2$, $C_3$, $C_{17}$, $C_{20}$, and/or $C_{29}$ positions of betulinic acid as described in the examples. The derivatives were characterised on the basis of spectral data. Table III to Table VIII refer to the structures shown in FIGS. 3 to 8 respectively and lists the structures of the twenty-seven derivatives mentioned in Table II.

FIG. 3 of the accompanying drawings wherein R to $R_4$ are shown as follows:

TABLE III

| DERIVATIVE | R | $R_1$ | $R_2$ | $R_3$ | $R_4$ |
|---|---|---|---|---|---|
| MJ321-RS | H | H | H | O—CO—CH$_3$ | H |
| MJ398-RS | H | H | H | O—CO—CH(OCOCH$_3$)—CH$_3$ | H |
| MJ408-RS | H | H | H | O—CO—CH$_3$ | CH$_2$COOCH$_3$ |
| MJ417-RS | H | H | H | OH | CH$_2$COOCH$_3$ |
| MJ434-RS | H | H | H | O—CO—C(CH$_3$)$_3$ | H |
| MJ443-RS | H | H | H | OH | CH$_2$COOH |
| MJ457-RS | H | H | H | O—CO—CH(OCOCH$_3$)—CH$_3$ | CH$_2$—COOCH$_3$ |
| MJ529-RS | H | H | H | O—CO—CH$_2$—CH$_3$ | H |
| MJ580-RS | H | H | H | OCOC$_6$H$_5$ | H |
| MJ677-RS | H | H | H | NH$_2$ | H |
| MJ739-RS | H | H | H | OCOCH(OCOCH$_3$)C$_6$H$_5$ | H |

FIG. 4 of the accompanying drawings wherein R to $R_4$ are shown as follows:

TABLE IV

| DERIVATIVE | R | $R_1$ | $R_2$ | $R_3$ | $R_4$ |
|---|---|---|---|---|---|
| MJ455-RS | H | H | H | O-CO-CH$_3$ | H |
| MJ458-RS | H | H | H | OH | H |
| MJ462-RS | H | H | H | O—CO—CH(OCOCH$_3$)—CH$_3$ | H |
| MJ525-RS | H | H | H | O—COCH(OCOCH$_3$)—CH$_3$ | CH$_2$COOCH$_3$ |
| MJ577-RS | H | H | H | OH | CH$_2$COOH |
| MJ606-RS | H | H | H | OCOC$_6$H$_5$ | H |

FIG. 5 of the accompanying drawings wherein R to $R_3$ are shown as follows:

TABLE V

| DERIVATIVE | R | $R_1$ | $R_2$ | $R_3$ |
|---|---|---|---|---|
| MJ347-RS | H | H | O | H |
| MJ351-RS | H | H | N—OH | H |
| MJ353-RS | H | H | N—NH—Ph | H |
| MJ438-RS | H | H | N—OH | CH$_2$COOCH$_3$ |
| MJ481-RS | H | H | N—O—CO—CH$_3$ | H |
| MJ484-RS | H | H | N—O—SO$_2$—C$_6$H$_4$CH$_3$ | H |
| MJ623-RS | H | H | NNHC$_6$H$_4$OCH$_3$ | H |

FIG. 6 of the accompanying drawings wherein R to $R_3$ are shown as follows:

TABLE VI

| DERIVATIVE | R | $R_1$ | $R_2$ | $R_3$ |
|---|---|---|---|---|
| MJ463-RS | H | H | N—OH | H |
| MJ487-RS | H | H | N—NH—Ph | H |
| MJ586-RS | H | H | NNHC$_6$H$_2$Cl$_3$ | H |
| MJ617-RS | H | H | NNHC$_6$H$_4$OCH$_3$ | H |
| MJ717-RS | H | H | NNHC$_6$H$_3$(Br) (OCH$_3$) | H |

FIG. 7 of the accompanying drawings wherein R to $R_5$ are shown as follows:

TABLE VII

| DERIVATIVE | R | $R_1$ | $R_2$ | $R_3$ | $R_4$ | $R_5$ |
|---|---|---|---|---|---|---|
| MJ352-RS | H | Br | O | H | Br | Br |
| MJ524-RS | H | Br | O | $CH_2COOCH_3$ | Br | Br |
| MJ527-RS | H | Br | O | $CH_2$—COO—$CH_3$ | H | H |
| MJ542-RS | H | Br | O | H | H | H |
| MJ548-RS | H | Br | O | $CH_2CH_2COOCH_3$ | H | H |
| MJ719-RS | H | H | $NNHC_6H_3$ $(Br)(OCH_3)$ | H | H | Br |

FIG. 8 of the accompanying drawings wherein R to $R_6$ are shown as follows:

TABLE VIII

| DERIVATIVE | R | $R_1$ | $R_2$ | $R_3$ | $R_4$ | $R_5$ | $R_6$ |
|---|---|---|---|---|---|---|---|
| MJ544B-RS | H | Br | H | OH | H | Br | Br |
| MJ549-RS | H | H | H | O—CO—$CH_3$ | H | Br | Br |
| MJ568-RS | H | Br | H | OH | H | H | H |
| MJ631-RS | H | Br | H | OH | $CH_2COOCH_3$ | H | H |
| MJ635-RS | H | Br | H | OH | $CH_2COOH$ | H | H |
| MJ671-RS | H | H | H | OH | H | Br | Br |
| MJ681-RS | H | H | H | $OCOCH_3$ | $CH_2COOCH_3$ | Br | Br |

EXAMPLE 16

Betulinic acid is known to exert its anti-melanoma activity by causing apoptosis (programmed cell death). Apoptosis culminates in the fragmentation of the cellular DNA which can be detected by using monoclonal antibodies to the fragmented DNA (mono and polyoligonucleosomes). Apoptosis may be used as an indicator for specific cytotoxicity of the test compound. Apoptosis was investigated as a probable (or one of the probable) mechanisms of action of betulinic acid for killing leukemia cells (MOLT-4). Briefly, cells were treated with 5 μg/ml of betulinic acid or its derivatives in vitro and incubated at 37° C. in a $CO_2$ incubator for 24 hours, 48 hours or 72 hours. Untreated cells served as controls. At the end of the incubation, one-half of the cells were lysed with lysis buffer after removing the supernatant. The supernatant of the remaining cells was collected without lysing the cells. Both lysate and supernatant were centrifuged at 16,000 rpm to separate intact DNA from fragmented DNA, if any. The supernatants were assayed for DNA fragments while the pellets containing intact DNA were discarded. The DNA fragments were detected by a commercially available kit (Boehringer Mannheim, Cat 1774425) in culture supernatants but not in the lysates indicating the presence of fragmented DNA in culture supernatant followed by the lysis of treated cells. The DNA fragments were not detected in untreated cells or cells treated with 5 μg/ml of betulinic acid/betulinic acid derivatives for 24 hours or 48 hours. This suggests that the process of apoptosis occurs between 48 hours and 72 hours of drug treatment.

Table IX shows the Enrichment factor of apoptosis for betulinic acid and its derivatives against MOLT-4 leukemia cells.

TABLE IX

| | Enrichment Factor | | | | | |
|---|---|---|---|---|---|---|
| Cell line | MJ321-RS | MJ351-RS | MJ352-RS | MJ353-RS | Betulinic acid | MJ398-RS |
| MOLT-4 | 5.63 | 3.33 | −0.03 | 10.07 | 15.19 | ND* |

*Not Done

The Enrichment factor is calculated by the formula:

$$\text{Enrichment factor} = \frac{\text{mU of the Sample(dying/dead cells)}}{\text{mU of the corresponding Control cells(cells without treatment)}}$$

All derivatives show Enrichment factor less than betulinic acid indicating varying degrees of apoptosis.

EXAMPLE 17

A suitable formulation of betulinic acid or its derivatives was prepared as follows. Betulinic acid or its derivatives were solubilized in a minimum volume of methanol. Betulinic acid or its derivatives may also be solubilized in isopropyl alcohol, dimethylformamide, dimethylsulfoxide or any other suitable solvent. Polyvinylpyrolidone was separately solubilized in methanol or a suitable solvent. Both were mixed and evaporated at 30–100° C. under vacuum while being stirred continuously. A fluffy mass was obtained which solubilized in water at a concentration of 0.1 to 50 mg per milliliter of water [preferably 1–20 mg betulinic acid (or its derivatives) per milliliter of water]. Betulinic acid (or its derivatives) to PVP ratio was between 1:1 to 1:20 (preferably between 1:2 to 1:10).

Systemic administration refers to oral, rectal, nasal, transdermal and parental (i.e., intramuscular, intraperitoneal, subcutaneous or intravenous). In accordance with good clinical practice, it is preferred to administer the composition at a dose that will produce anticancer effects without causing undue harmful side effects. The composition may be administered either alone or as a mixture with other therapeutic agents.

The compositions of this invention may contain betulinic acid alone, one or more betulinic acid derivatives alone; or betulinic acid and one or more betulinic acid derivatives.

The composition may optionally and preferably contain pharmaceutically acceptable diluents, fillers, lubricants, excipients, solvents, binders, stabilizers, and the like. The preferred diluents may be selected from lactose, starch, mannitol, sorbitol, microcrystalline cellulose, dibasic calcium phosphate dihydrate, sucrose, calcium sulfate dihydrate, dextrose, inositol, maltose and amylose; the preferred binders may be selected from maize starch, wheat starch, rice starch, potato starch, gelatin, tragacanth, methyl cellulose, hydroxy propyl methyl cellulose, sodium carboxy methyl cellulose and polyvinyl pyrolidone; the preferred fillers may be selected from lactose, sucrose, mannitol, sorbitol, calcium phosphates; the preferred lubricants may be selected from silica, talc, stearate acid or salts thereof such as magnesium stearate, or calcium stearate, and/or polyethylene gylcol.

Pharmaceutical compositions which provide from about 10 mg to 1000 mg of the composition per unit dose are preferred and are prepared as tablets, lozenges, capsules, powders, aqueous or oily suspensions, syrups, elixirs, implants or aqueous solutions by any conventional method. The nature of the pharmaceutical composition employed will, of course, depend on the desired route of administration. The human dosage of the composition is in the range of 10 to 200 mg/kg/day and the preferred range is 20 to 50 mg/kg/day.

EXAMPLE 18

The acute toxicity study of betulinic acid and its derivatives MJ398-RS, MJ438-RS and MJ542-RS was carried out on 10–12 week old BALB/C mice weighing approximately 25 grams. All animals were acclimatized for 7 days and were fasted 18 hours before and 4 hours after dosing. All experimental animals were observed for 5 days. Observations were made three times on the day of dosing and twice daily thereafter for the remaining 5 days or until reversible toxic signs (if any) subsided. Acute intraperitoneal toxicity study was conducted at three different dose levels of 200 mg/Kg body Wt., 400 mg/Kg body Wt and 600 mg/Kg body Wt. for betulinic acid, three dose levels of 500 mg/Kg body Wt., 750 mg/Kg body Wt and 1000 mg/Kg body Wt. for MJ398-RS and MJ438-RS and three dose levels of 200 mg/Kg body Wt., 400 mg/Kg body Wt and 800 mg/Kg body Wt. for MJ542-RS to calculate $LD_{50}$ value. No mortality was recorded in betulinic acid and MJ542-RS. There was no visible toxicity or weight loss. hence the $LD_{50}$ of betulinic acid is greater than 600 mg/Kg body Wt. and the $LD)_{50}$ of MJ542-RS is greater than 800 mg/Kg body Wt. The $LD_{50}$ for MJ398-RS and MJ438-RS was 750 mg/Kg body Wt.

EXAMPLE 19

To test the in vivo ability of betulinic acid to serve as an anticancer agent against leukemia, studies were performed with 6 week old athymic mice each weighing approximately 25 g, injected subcutaneously with approximately 20 million leukemia cells (MOLT-4). Drug treatment with betulinic acid was initiated on day one, i.e., 24 hours post-injection of MOLT-4 cells. Betulinic acid was co-precipitated with polyvinylpyrolidone to increase solubility and bioavailability (Waller, D. P., et al Contraception 22, 183–187, 1980). Six animals were treated with the drug at a dose of 40 mg/kg body weight. A total of six intraperitoneal injections were given every alternate day. Four control animals were treated with the vehicle alone. The mice were weighed and the tumors measured with a vernier calliper every alternate day. The treatment resulted in complete inhibition of tumor growth as compared with the control animals which attained a tumor volume of approximately 900 mm³ by day 30.

EXAMPLE 20

The effect of betulinic acid was determined on normal cell metabolism in vitro. The panel of normal cells included normal mouse splenocytes, and lung fibroblasts (MRC-9, passage number 4). A 72-hour MTT cytotoxicity assay was performed as described previously. In each of the cell lines, the $ED_{50}$ value of betulinic acid was determined to be greater than 20 μg/ml indicating non toxicity of betulinic acid to normal cells.

The instant invention is shown and described herein in what is considered to be the most practical, and preferred embodiments. It is recognized, however, that departures may be made therefrom which are within the scope of the invention, and that obvious modifications will occur to one skilled in the art upon reading this disclosure.

We claim:
1. A betulinic acid derivative of formula 2

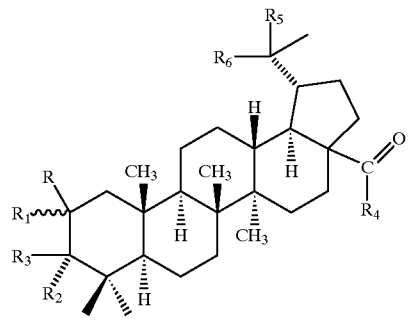

wherein R, $R_1$, $R_2$, $R_3$, $R_4$, $R_5$ and $R_6$ independently or in combination represent:

R is H;

$R_1$ is H, Br, Cl, F or I;

$R_2$ and $R_3$ together are $NNHC_6H_5$, $NNHC_6H_2Cl_3$, $NNHC_6H_4OCH_3$, $NNHC_6H_4OH$, or $NNHC_6H_3(Br)$ $(OCH_3)$;

$R_4$ is OH, $—OCH_3$, $O(CH_2)_nCOOCH_3$, $O(CH_2)_n$ $COOC_2H_5$, $O(CH_2)_nCOOH$, $O(CH_2)_nCOCl$ (where n=1 to 5), $OCH_2CH_2OC_2H_5$, $OCH_2CH_2OH$, $OCH_2CH_2OCOCH_3$, Cl, $N_3$, $NHNH_2$, $HNNHC_6H_4OMe$, $NHNHC_6H_2Cl_3$, $NH_2$, or $NH(CH_2)_n$ $CH_3$ (where n=0 to 9);

$R_5$ is H and;

$R_6$ is $CH_3$, or pharmaceutically acceptable salts thereof.

2. A derivative as claimed in claim 1 wherein the derivative is of formula 6

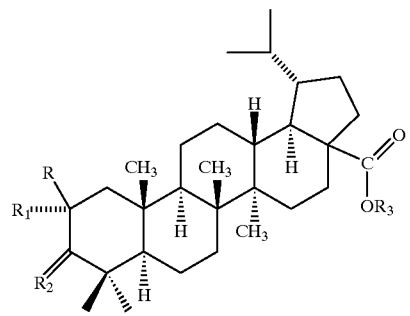

wherein R=H; $R_1$=H; $R_2$=$NNHC_6H_2Cl_3$, $NNHC_6H_4OCH_3$, $NNHC_6H_3(Br)(OCH_3)$ or $NNHC_6H_5$; and $R_3$=H.

3. A composition comprising a betulinic acid derivative of claim 1 and a pharmaceutically acceptable additive, diluent, excipient, solvent, binder, stabilizer, carrier, filler or lubricant.

4. A composition comprising a betulinic acid derivative of claim 2 and a pharmaceutically acceptable additive, diluent, excipient, solvent, binder, stabilizer, carrier, filler or lubricant.

5. A composition as claimed in claim 3 which provides 10 mg to 1000 mg per unit dose of betulinic acid derivative.

6. A composition as claimed in claim 4 which provides 10 mg to 1000 mg per unit dose of betulinic acid derivative.

7. A method of treating a patient with leukemia or lymphoma or prostate, lung or ovarian cancer said method comprising administering a pharmaceutically effective dosage of a betulinic acid derivative of formula 2 or a pharmaceutically acceptable salt thereof,

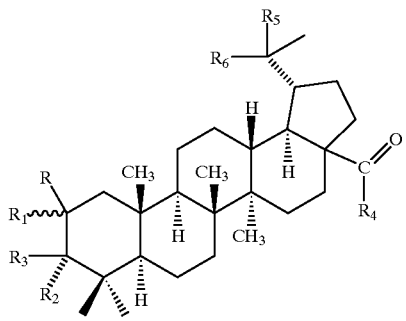

wherein R, $R_1$, $R_2$, $R_3$, $R_4$, $R_5$ and $R_6$ independently or in combination represent:

R is H;
$R_1$ is H, Br, Cl, F or I;
$R_2$ and $R_3$ together are $NNHC_6H_5$, $NNHC_6H_2Cl_3$, $NNHC_6H_4OCH_3$, $NNHC_6H_4OH$, or $NNHC_6H_3(Br)(OCH_3)$;
$R_4$ is OH, —$OCH_3$, $O(CH_2)_nCOOCH_3$, $O(CH_2)_nCOOC_2H_5$, $O(CH_2)_nCOOH$, $O(CH_2)_nCOCl$ (where n=1 to 5), $OCH_2CH_2OC_2H_5$, $OCH_2CH_2OH$, $OCH_2CH_2OCOCH_3$, Cl, $N_3$, $NHNH_2$, $HNNHC_6H_4OMe$, $NHNHC_6H_2Cl_3$, $NH_2$, or $NH(CH_2)_nCH_3$ (where n=0 to 9);
$R_5$ is H; and
$R_6$ is $CH_3$ to a patient in need thereof.

8. A method as claimed in claim 7 wherein said patient is a human, mammal or other animal.

9. A method as claimed in claim 7 wherein $ED_{50}$ value of betulinic acid derivative against prostate cancer is 1.13±0.35 µg/ml.

10. A method as claimed in claim 7 wherein $ED_{50}$ value of betulinic acid derivative against leukemia or lymphoma is in the range of 0.5 to 4.0 µg/ml.

11. A method as claimed in claim 7 wherein $ED_{50}$ value of betulinic acid derivative against prostate cancer in the range of 1.1 to 6.8 µg/ml.

12. A method as claimed in claim 7 wherein $ED_{50}$ value of betulinic acid derivative against ovarian cancer is in the range of 0.4 to 8.1 µg/ml.

13. A method as claimed in claim 7 wherein the betulinic acid derivative is administered to the patient in a pharmaceutically acceptable additive, carrier, diluent, solvent, filler, lubricant, excipient, binder or stabilizer.

14. A method as claimed in claim 7 wherein the betulinic acid derivative is administered in the form of a tablet, lozenge, capsule, powder, aqueous or oily suspension, syrup, elixir, implant or aqueous solution.

15. A method as claimed in claim 8 wherein the dosage for humans is in the range of 10 to 200 mg/kg/day.

16. A method as claimed in claim 7 wherein the dosage is in the range of 20 to 50 mg/kg/day.

17. A method as claimed in claim 7 wherein the betulinic acid derivative is administered to the patient systemically.

18. The method according to claim 7 for the treatment of leukemia.

19. The method according to claim 7 for the treatment of lymphoma.

20. The method according to claim 7 for the treatment of prostate cancer.

21. The method according to claim 7 for the treatment of lung cancer.

22. The method according to claim 7 for the treatment of ovarian cancer.

23. A method of treating a patient with leukemia or lymphoma or prostate, lung or ovarian cancer said method comprising administering a pharmaceutically effective dosage of a betulinic acid derivative of formula 6,

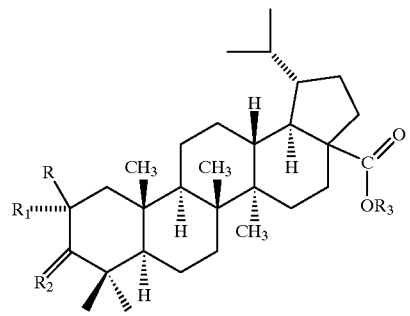

wherein R=H; $R_1$=H: $R_2$=$NNHC_6H_2Cl_3$, $NNHC_6H_4OCH_3$, $NNHC_6H_3(Br)(OCH_3)$ or $NNHC_6H_5$; and $R_3$=H.

24. A method as claimed in claim 23 wherein said patient is a human, mammal or other animal.

25. A method as claimed in claim 23 wherein the betulinic acid derivative is administered to the patient in a pharmaceutically acceptable additive, carrier, diluent, solvent, filler, lubricant, excipient, binder or stabilizer.

26. A method as claimed in claim 24 wherein the betulinic acid derivative is administered in the form of a tablet, lozenge, capsule, powder, aqueous or oily suspension, syrup, elixir, implant or aqueous solution.

27. A method as claimed in claim 24 wherein the dosage for humans is in the range of 10 to 200 mg/kg/day.

28. A method as claimed in claim 23 wherein the dosage is in the range of 20 to 50 mg/kg/day.

29. A method as claimed in claim 23 wherein the betulinic acid derivative is administered to the patient systemically.

30. The method according to claim 23 for the treatment of leukemia.

31. The method according to claim 23 for the treatment of lung cancer lymphoma.

32. The method according to claim 23 for the treatment of prostate cancer.

33. The method according to claim 23 for the treatment of lung cancer.

34. The method according to claim 23 for the treatment of ovarian cancer.

* * * * *